US00PP25499P3

(12) United States Plant Patent
Olesen

(10) Patent No.: US PP25,499 P3
(45) Date of Patent: May 5, 2015

(54) MINIATURE ROSE PLANT NAMED 'POULPAL050'

(50) Latin Name: ***Rosa* hybrid**
Varietal Denomination: Poulpal050

(71) Applicant: Mogens Nyegaard Olesen, Fredensborg (DK)

(72) Inventor: Mogens Nyegaard Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 102 days.

(21) Appl. No.: 13/986,933

(22) Filed: Jun. 14, 2013

(65) Prior Publication Data

US 2014/0373220 P1 Dec. 18, 2014

(51) Int. Cl.
*A01H 5/00* (2006.01)

(52) U.S. Cl.
USPC ..... Plt./122

(58) Field of Classification Search
USPC ..... Plt./122, 129
See application file for complete search history.

*Primary Examiner* — Kent L Bell

(57) ABSTRACT

A new miniature rose plant that has abundant, red flowers and attractive foliage. The variety successfully propagates from softwood cuttings and is suitable for year-round production in commercial glasshouses. This new and distinct variety has shown to be uniform and stable in the resulting generations from asexual propagation.

2 Drawing Sheets

Botanical designation: *Rosa* hybrid.
Variety denomination: 'Poulpal050'.

SUMMARY OF THE INVENTION

The present invention constitutes a new and distinct variety of miniature rose plant which originated from a controlled crossing between the female seed parent, an unnamed seedling, and the male pollen parent, also an unnamed seedling.

The two parents were crossed during the summer of 2007 and the resulting seeds were planted in a controlled environment in Fredensborg, Denmark. The new variety, named 'Poulpal050', originated as a single seedling from the stated cross.

The new variety may be distinguished from its male pollen parent and female seed parent primarily by flower coloration and growth habit.

The objective of the hybridization of this rose variety for commercial culture was to create a new and distinct variety with unique qualities, such as:

1. Uniform and abundant red flowers;
2. Vigorous and compact growth;
3. Year-round flowering under glasshouse conditions;
4. Suitability for production from softwood cuttings in pots;
5. Durable flowers and foliage which make a variety suitable for distribution in the floral industry.

This combination of qualities is not present in previously available commercial cultivars of this type, known to the inventor, and distinguish 'Poulpal050' from all other varieties of which we are aware.

As part of the rose development program, Mogens N. Olesen germinated the seeds from the aforementioned hybridization and conducted evaluations on the resulting seedlings in a controlled environment in Fredensborg, Denmark. 'Poulpal050' was selected by the inventor as a single plant from the progeny of the hybridization in 2007.

Asexual reproduction of 'Poulpal050' by cuttings was first done by Mogens N. Olesen in the nursery in Fredensborg, Denmark in 2008. This initial and other subsequent propagations conducted in controlled environments have demonstrated that the characteristics of 'Poulpal050' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulpal050'.

Specifically illustrated in FIG. 1 are the flowers at various stages of development, flower in parts, mature leaves, and stems.

DETAILED DESCRIPTION OF THE VARIETY

Figure 1:
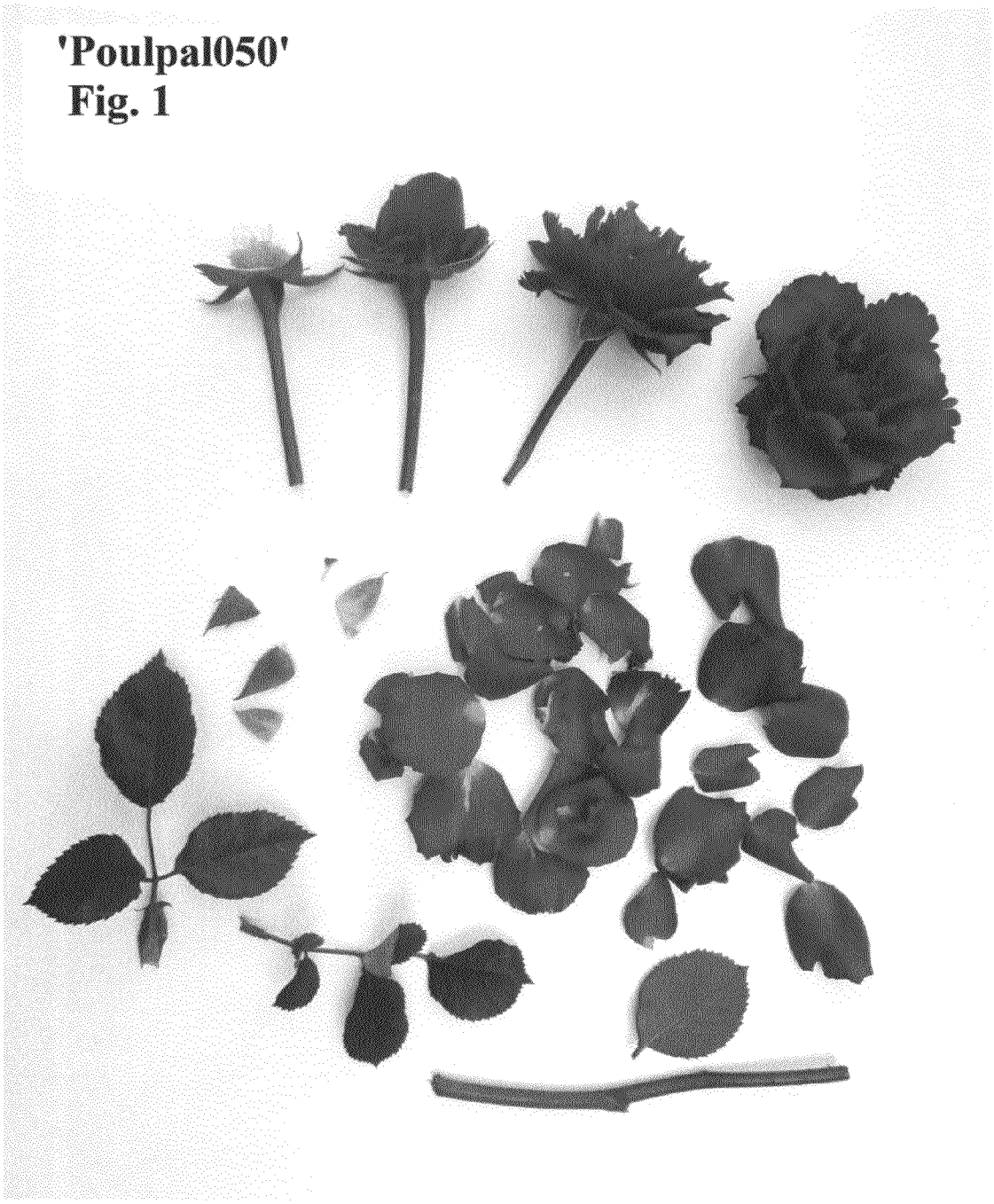
Figure 2:
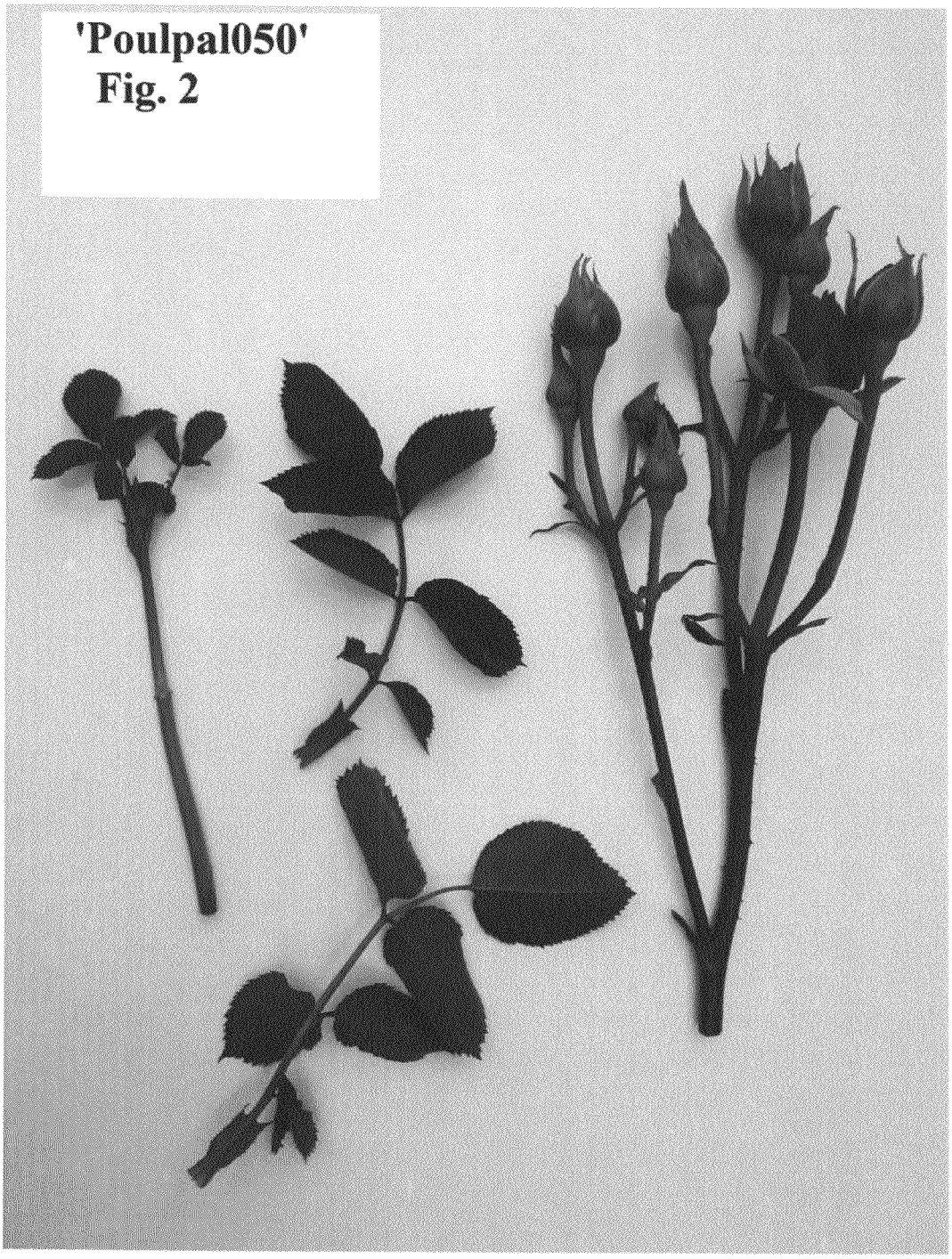
FIG. 2 demonstrates juvenile leaves, stems, and flower buds.

The following is a description of 'Poulpal050', as observed in its growth in a field nursery in Benton County Oreg. Observed plants are 10 months of age and were cultivated on their own roots. Color references are made using The Royal Horticultural Society (London, England) Colour Chart, 2001, except where common terms of color are used.

For a comparison, several physical characteristics of the rose variety 'Poulchris', U.S. Plant Pat. No. 11,151 are compared to 'Poulpal050' in Chart 1.

CHART 1

| | 'Poulpal050' | 'Poulchris' |
|---|---|---|
| Petalage: | 55 | 55-65 |
| Flower Diameter: | 70 mm | 60 mm |
| Petal Color, After | Red Group 46A and | Upper Red 53 A |

CHART 1-continued

| | 'Poulpal050' | 'Poulchris' |
|---|---|---|
| Opening | 46B on the upper surface with a petal spot Yellow Group 6C. Red Group 46A with intonations of Red-Purple Group 59C on the lower surface. Lower surface petal spots are White Group 155A. | Lower Red 53 C |

FLOWER AND FLOWER BUD

Blooming habit: Continuous.

Flower bud:

*Size*.—Upon opening, 32 mm in length from base of receptacle to end of bud. 19 mm in diameter.

*Bud form*.—Urceolate.

*Bud color*.—As sepals unfold, petals are Red Group 53A with intonations of Greyed-Purple Group 185A.

*Sepals*.—Upper Surface: Color: Yellow-Green Group 147C. Texture: Smooth, moderately pubescent. Lower Surface: Color: Yellow Green Group 144A with strong intonations of Greyed-Red Group 178A. Texture: Somewhat rough. Shape: Apex: Cirrhose. Base: Flat at union with receptacle. Margins: Margins have weak foliaceous appendages on three of the five sepals. Size: 25 mm long by 11 mm wide.

*Receptacle*.—Surface Texture: Smooth. Shape: Campanulate. Size: 10 mm tall and 10 mm wide. Color: Yellow-Green Group 144A with intonations of Greyed-Orange Group 176A.

*Pedicel*.—Surface: Smooth. Length: 50 mm on average. Diameter: Generally 3 to 4 mm. Color: Yellow-Green Group 146C with intonations of Greyed-Red Group 178A. Strength: Strong. Borne: Singly or in clusters of 3 to 5 flowers per branch.

*Peduncles*.—Surface: Smooth. Length: 2 to 10 cm on average. Diameter: Generally 3 to 4 mm. Color: Yellow-Green Group 146C with intonations of Greyed-Red Group 178A.

Flower bloom:

*Fragrance*.—None.

*Duration*.—As a pot plant, flowers last up to 24 days.

*Size*.—Flower diameter is 70 mm when open. Flower depth is 30 mm.

*Form*.—General shape is a hybrid tea with a high pointed center. Fully open flowers from an open cup.

*Shape of flower, side view*.—The upper portion is a flattened convex. The lower portion is a concave.

Petalage: Under normal conditions, flowers have 55 petals total, 5 to 7 of which are petaloids.

Color:

*General tonality*.—On open flower Red Group 46A to 46B.

*Upon opening, petals*.—Outermost and innermost petals are Red Group 46B on the upper surface. Red Group 53A to 53B on the lower surface. Some guard petals have intonations of Yellow-Green Group 146C on the lower surface. At the base of the petal lower surface, Red Group 38B. The upper surface petal spot is Yellow Group 6C.

*After opening, petals*.—Outermost and innermost petals are Red Group 46A and 46B on the upper surface with a petal spot Yellow Group 6C. Red Group 46A with intonations of Red-Purple Group 59C on the lower surface. Lower surface petal spots are White Group 155A.

Petals:

*Petal reflex*.—Slightly reflexed inward.

*Margin*.—As the flowers open, margins are entire. After opening, undulations are very strong, and there are numerous clefts.

*Shape*.—Generally broad and elliptic. Apex shape: Rounded. Base shape: Rounded.

*Size*.—35 mm (l) by 42 mm (w).

*Texture*.—Smooth.

*Thickness*.—Thick.

Petaloids:

*Quantity*.—5 to 7 on average.

*Shape*.—Irregular, and asymmetric. The apex and base are acute.

*Color*.—Red Group 46A and 46B on the upper surface with a petal spot Yellow Group 6C. Red Group 46A with intonations of Red-Purple Group 59C on the lower surface.

*Size*.—10 mm (l) by 8 mm (w).

Reproductive organs:

*Pollen*.—None Observed.

*Anthers*.—Size: 2 mm long. Color: Yellow Group 10A with intonations of Yellow-Orange Group 15A. Quantity: 65 on average.

*Filaments*.—Color: Yellow Group 3A. Length: About 4 mm.

*Pistils*.—Length: About 7 mm long. Quantity: 24 on average.

*Stigmas*.—Slightly superior relative to the length of the filaments and the height of the anthers. Color: Greyed-Yellow Group 160D.

*Styles*.—Color: Greyed-Yellow Group 160D.

*Seed formation*.—Not observed.

PLANT

Plant growth: Upright. Plants are about 40 cm in height, and 35 to 40 cm wide.

Stems:

*Color*.—Juvenile growth: Yellow-Green Group 146C with intonations of Greyed-Orange Group 174A. Mature growth: Yellow-Green Group 146B.

*Length*.—Canes are 30 cm from the base of the plant to the flowering portion.

*Diameter*.—7 mm.

*Internodes*.—On mature canes, there is an average distance of 35 to 50 mm between nodes.

*Surface texture*.—Young wood is smooth. Mature wood has small and large prickles.

Large prickles:

*Incidence*.—2 per 10 cm of stem.

*Size*.—Average length: 3 to 4 mm.

*Color*.—Juvenile prickles are Greyed-Purple Group 185A. Mature prickles are Greyed-Yellow Group 160D.

*Shape*.—Upper portion is linear. Deep concave on lower side.

Plant foliage:

*Compound leaf size.*—90 to 150 mm (l) by 65 to 100 mm (w).

*Quantity.*—2 leaves per 10 cm of stem.

*Color of juvenile foliage.*—Upper Leaf Surface: Greyed-Purple Group 187A. Lower Leaf Surface: Greyed-Purple Group 187A.

*Color of mature foliage.*—Upper Leaf Surface: Yellow-Green Group 147A. Lower Leaf Surface: Yellow-Green Group 147B.

Plant leaves and leaflets:

*Stipules.*—Size: About 15 mm in length. Shape: Linear, slightly broad based with outward extending species. Margins: Finely serrated with few stipitate glands. Color: Greyed-Purple Group 183B with Yellow-Green Group 144B.

*Petiole.*—Length: 23 mm on average. Diameter: About 2 mm. Upper surface: Yellow-Green Group 144A. Lower surface: Yellow-Green Group 144A with Greyed-Purple Group 183A.

*Rachis.*—Length: 65 to 75 mm. Diameter: About 2 mm. Upper surface: Yellow-Green Group 144A. Lower surface: Yellow-Green Group 144A with Greyed-Purple Group 183A. Small prickles observed.

*Leaflet.*—Number of leaflets: 5 on normal leaves in middle of the stem. Size: 45 mm in length by 40 mm wide. Margin: Serrate. General Shape: Rounded. Apex Shape: Mucronate. Base Shape: Round. Texture: Smooth. Arrangement: Odd pinnate. Venation: Reticulate. Leaf Gloss: Moderately glossy.

Cold hardiness: The variety is tolerant to USDA Cold Hardiness Zone 6.

Heat tolerance: The variety has been found to be suitable for climate conditions found in the American Horticulture Society heat zone 7.

The invention claimed is:

1. A new and distinct variety of rose plant of the miniature class named 'Poulpal050', substantially as illustrated and described herein, due to its abundant, red flowers, vigorous growth, compact habit, suitability for production from softwood cuttings in pots, and durable flowers and foliage that make the variety suitable for distribution in the floral industry.

* * * * *

'Poulpal050'

'Poulpal050'